United States Patent [19]

Folkers et al.

[11] Patent Number: 4,656,247

[45] Date of Patent: Apr. 7, 1987

[54] EFFECTIVE HORMONAL PEPTIDES: D-3-QA1 6-LHRH

[75] Inventors: Karl Folkers, Austin, Tex.; Xu Jie-Cheng, Shanghai, China; Cyril Y. Bowers, New Orleans, La.

[73] Assignee: Board of Regents, The University of Texas System, Austin, Tex.

[21] Appl. No.: 727,710

[22] Filed: Apr. 26, 1985

[51] Int. Cl.$^4$ ................................................ C07K 7/20
[52] U.S. Cl. ................................................ 530/313
[58] Field of Search ............... 260/112.5 LH; 530/313

[56] References Cited

U.S. PATENT DOCUMENTS

| | | | |
|---|---|---|---|
| 3,655,636 | 4/1972 | Young | 260/112.5 |
| 4,234,571 | 11/1980 | Nestor et al. | 260/112.5 LH |
| 4,310,517 | 1/1982 | Etschenberg et al. | 424/177 |
| 4,504,414 | 3/1985 | Folkers et al. | 260/112.5 |

OTHER PUBLICATIONS

G. Tolis, et al., "Tumor Growth Inhibition in Patients with Prostatic Carcinoma Treated with Luteinizing Hormone-Releasing Hormone Agonists," *Proc. Natl. Acad. Sci. USA* 79: 1658–1662 (Mar. 1982).
D. H. Coy, "Peptide Antagonists of LHRH: Large Increases in Anti-Ovulatory Activities Produced by Basic D-Amino Acids in the Six Position," *Endocrinol.* 110: 1445–1447 (1982).
J. J. Nestor, "Synthesis and Biological Activity of Some Very Hydrophobic Superagonist Analogues of Luteinizing Hormone-Releasing Hormone," *J. Med. Chem.* 25: 795–801 (1982).
J. Humphries, et al., "Structural Requirements in Positions 1, 2, 3 and 6 of the Luteinizing Hormone-Releasing Hormone (LHRH) for Antiovulations Activity," *J. Med. Chem.* 22: 774–777 (1979).
M. U. Nekola, "Suppression of Ovulation in the Rat by an Orally Active Antagonist of Luteinizing Hormone-Releasing Hormone," *Science* 218: 160–162 (Oct. 8, 1982).
A. U. Schally, "Antitumor Effects of Analogs of Hypothalomic Hormones in Endocrine-Dependent Cancers," *Proc. Soc. Exp. Bio. Med.* 175: 259–281 (1984).
Marshall et al., *Proceedings of the Society for Experimental Biology and Medicine,* 149, 351–355 (1975).

*Primary Examiner*—Donald B. Moyer
*Assistant Examiner*—F. T. Moezie
*Attorney, Agent, or Firm*—Arnold, White & Durkee

[57] ABSTRACT

Two sets of hormonal peptides are synthesized which are super agonists of the lutenizing hormone releasing hormone (LHRH). Chronic administration results in the inhibition of LHRH which is responsible for stimulating cell growth in the testes. One peptide has the D(dextro)-form of a mono-heterocyclic amino acid in position six (D-3-pyridyl-alanine) while the other peptide has a bi-heterocyclic amino acid in that same position ($\beta$-(3-quinolyl)-D-$\alpha$-alanine). Both peptides are less metabolically reactive than those in the prior art and yet both peptides are significantly more potent than LHRH itself.

4 Claims, No Drawings

EFFECTIVE HORMONAL PEPTIDES: D-3-QA1 6-LHRH

BACKGROUND OF THE INVENTION

This invention concerns synthetic analogs of the peptide hormone known as the leutinizing hormone releasing hormone (LHRH). These analogs have biological potency superior to that of the LHRH which exists naturally in the hypothalamus of the human brain.

PROSTATE CANCER

Carcinoma of the prostate is the second leading cause of cancer-related deaths for adult American males who are generally over 55 years of age. About 70% of all cases of prostatic neoplasms are hormone-dependent or androgen-dependent. Prolactin may be a promoter of prostate growth. The medical treatment of prostate cancer emphasizes surgery and the therapeutic administration of estrogens and antiangrogens. Surgical castration is associated with both psychological and physiological side effects which can be extraordinarily serious. The mortality from the cardiovascular disease associated with administration of estrogens and antiandrogens can be significantly high.

Other therapeutic treatments of prostatic cancer are not satisfactorily effective, and new treatments of great superiority for prostate and other hormone related cancers are urgently needed.

AN EMERGING NEW CHEMOTHERAPY FOR PROSTATE CANCER

The synthetic analogs of LHRH which can be up to 100 times more potent than the natural LHRH have become known as "super agonists" or "super active agonists" because of their high potency. The expression "agonist" designates the intrinsic activity of a natural hormone.

Groups of investigators conducting animal studies with these super agonists of LHRH observed that the administration caused decreases in the weights of the testes, seminal vesicles and the prostate, and decreases in testosterone levels and certain receptors.

In men, two such super agonists, known as $D\text{-Trp}^6$-LHRH and $D\text{-Ser}(Bu^t)^6$ $des\text{-Gly}^{10}\text{-NH}_2$-LHRH ethylamide were found to cause a suppression of Leydig cell function and decreases in serum levels of testosterone, dihydrotestosterone and estradiol. These reductions were observed after chronic administration of the super agonists.

CLINICAL TRIALS WITH LHRH SUPER AGONISTS IN MEN WITH PROSTATE CANCER

The observations of the effects of the super agonists of LHRH in the diverse animal studies led to clinical trials of these super agonists in men with prostate cancer in the hope that the control of prostate cancer would be far superior to any existing chemotherapy and particularly to surgery.

Apparently, the first successful palliative treatment of advanced prostatic carcinoma in man by super agonists of LHRH was carried out at the Royal Victoria Hospital in Montreal by *Tollis et al.* (Proc. Natl. Acad. Sci., USA, 79; 1658–1662 (1982). Both $D\text{-Trp}^6$-LHRH and $D\text{-Ser}(Bu^t)^6$ $des\text{-Gly}^{10}\text{-NH}_2$-LHRH were administered subcutaneously in daily doses of 100 g and 50 g, respectively. In patients with urinary obstruction, there was noticeable clinical improvement. In patients with more advanced prostatic disease, the pain from bone metastases was relieved.

This collaborative trial demonstrated for the first time that super active analogs of LHRH could be beneficial therapeutic agents for prostatic cancer, and that such therapy might avoid the psychological impact of castration, even unnecessary castration, as well as the cardiovascular, hepatic, and mammotropic side effects of estrogens.

These and numerous other related studies have been reviewed by Schally et al. (Proc. Soc. Exp. Biol. Med. 175; 259–281 (1984).

THE NEED FOR NEWER SUPER AGONISTS OF LHRH FOR TREATMENT OF PROSTATIC CANCER

Obviously, $D\text{-Trp}^6$-LHRH and $D\text{-Ser}(Bu^t)^6$ $des\text{-Gly}^{10}\text{-NH}_2$-LHRH and related super agonists such as $D\text{-Leu}^6$LHRH ethylamide had all been synthesized solely because such modifications of LHRH had higher potencies than that of LHRH itself to release the leutenizing hormone. The subsequent years of biological research of the super agonists, almost entirely in animals, unexpectedly led to the investigations of their possible use to treat prostate cancer. Actually, the acute administration of these super agonists to cause release of LH and FSH contrasts to the chronic administration which results in inhibitory effects. In this endocrinology, the inhibitory effects were paradoxical.

These past super agonists of LHRH had been fortuitously available for the prostate cancer studies in animals and in man. There is reason to believe that such fortuitous agonists will not be ultimately found to be the safest and the most effective agonists to treat prostate cancer in man.

Such analogs of LHRH are well known to have multiple endocrinological activities, and side effects, and chemical differences in stability, and enzymic breakdown when injected into man.

THE DISADVANTAGES OF CERTAIN SUPER AGONISTS OF LHRH

It is well known in peptide chemistry that certain peptides with a moiety (or more than one) of tryptophan may be unstable and discolor on storage under diverse conditions. For example, LHRH itself has $Trp^3$ and the super agonist, $D\text{-Trp}^6$-LHRH, has $Trp^3$ and $D\text{-Trp}^6$ or the super agonist has two moieties of tryptophan which increases sensitivity to oxidation and deterioration. For acceptable medical use, a chemotherapeutic agent must have necessary chemical stability. Therefore, $D\text{-Trp}^6$-LHRH does not necessarily have the high-level of necessary stability which is requisite in chemotherapy.

$D\text{-Ser}(Bu^t)^6 des\text{-Gly}^{10}\text{-NH}_2$-LHRH and $D\text{-Leu}^6$-$des\text{-Gly}^{10}\text{-NH}_2$-ethylamide are both analogs of LHRH in which glycine has been replaced by a moiety of ethylamide. Such agonists with an N-terminal ethylamide moiety had a, fleeting popularity in the field of LHRH agonists in the hope that the N-terminal of the peptide would be protected against enzymic cleavage and loss of activity. Although this aspect of enzymology is theoretically sound, such analogs may show unexpected side effects and may not necessarily be safe and effective for the treatment of prostate cancer in man over prolonged periods of time.

SUMMARY OF THE INVENTION

In this invention, two primary peptides were synthesized which have the D(dextro)-form of a monocyclic but heterocyclic amino acid in position 6 and a bicyclic but heterocyclic amino acid in position 6, respectively. The first peptide has a moiety of D-3-pyridyl-alanine in position 6 and the second peptide has the moiety of β-(3-quinolyl)-D-α-alanine in position 6. The abbreviation D-3-Pal is used for D-3-pyridylalanine and the abbreviation D-3-Qal is used for β-(3-quinolyl)-D-α-alanine.

Accordingly, these two peptides are:
I.  pyroGlu-His-Trp-Ser-Tyr-D-3-Pal-Leu-Arg-Pro-GlyNH$_2$
II. pyroGlu-His-Trp-Ser-Tyr-D-3-Qal-Leu-Arg-Pro-GlyNH$_2$ Both of these two new peptides, I, II, when tested biologically, were found to be significantly more potent than LHRH itself and, therefore, these two new peptides are truly super agonists.

DETAILED DESCRIPTIONS OF PREFERRED EMBODIMENTS

Abbreviations and Formulas

| | |
|---|---|
| n-BuOH: | n-butyl alcohol |
| HOAc: | acetic acid |
| CH$_3$CN: | acetonitrile |
| KH$_2$PO$_4$: | potassium phosphate |
| o-Cl—Z: | o-chlorobenzyloxycarbonyl |
| CH$_2$Cl$_2$: | dichloromethane |
| TFA: | trifluoroacetic acid |
| Et$_3$N: | triethylamine |
| DCC: | dicyclohexylcarbodiimide |
| DMF: | dimethylformamide |
| i-PrOH: | isopropyl alcohol |
| BOC: | t-butyloxycarbonyl |
| CoF$_3$: | cobalt(III) fluoride |
| HF: | hydrogen fluoride |
| EtOAc: | ethyl acetate |
| Aoc: | acyloxy carbonyl |
| Br—Z: | o-bromocarbobenzoxy |
| Tos: | P—toluenesulfonyl radical |
| GlnONP: | glutamine-o-nitrophenol |

The protected amino acids were purchased from Peninsula Laboratories, Inc., San Carlos, Calif., except for Boc-D-pCl-Phe when it was provided by the Southwest Foundation for Research and Education. ε-Amino functions were protected by the Boc-group, except for Arg which was protected by the Aoc-or the Boc-group. Sidechain functions were protected by o-Cl-Z for the ε-amino group of Lys, Tos for Arg and Br-Z for Tyr. The benzhydrylamine hydrochloride resin was purchased from Beckman Inc., Palo Alto, Calif. All solvents (except TFA and isopropanol) were distilled before use.

To test for homogeneity the peptides were chromatographed on precoated TLC plates (silica gel, Merck, Darmstadt) in the following solvent systems:
I. EtoAc:Pyr:HOAc:H$_2$O=5:5:1:3;
II. n-BuOH:EtOAc:HOAc:H$_2$O=2:2:1:1:;
III. n-BuOH:Pyr:HOAc:H$_2$O=30:30:6:24;
IV. n-BuOH:Pyr:HOAc:H$_2$O=50:33:1:40;
V. n-BuOH:HOAc:H$_2$O=4:1:2

The spots on the developed thin layer plates were detected with the chlorine o-tolidine reagent.

Synthesis of the Peptides

The peptides were synthesized by the solid phase method using a Beckman Model 990 Peptide Synthesizer. The benzhydrylamine hydrochloride resin (BHA-resin) was used as a solid support. The program of the synthesizer was divided into subprograms to increase the versatility of the synthesizer, as follows:

1. Deprotection: 1. CH$_2$Cl$_2$ (2×wash, 1 or 2 min); 2. 50% TFA in CH$_2$Cl$_2$ containing 0.1% indole (1×wash, 1 or 2 min); 3. 50% TFA in CH$_2$Cl$_2$ containing 0.1% indole (deprotection, 20 min); 4. CH$_2$Cl$_2$ (2×wash).

2. Neutralization: 1. CH$_2$Cl$_2$ (2×wash, 1 or 2 min); 2. Et$_3$N (10% in CH$_2$Cl$_2$) (2×wash, 1 or 2 min); 3. Et$_3$N (10% in CH$_2$Cl$_2$) (neutralization, 5 min); 4. CH$_2$Cl$_2$ (2×wash, 1 or 2 min).

3. DCC Coupling: 1. CH$_2$Cl$_2$ (2×wash, 1 or 2 min); 2. amino acid solution in CH$_2$Cl$_2$ (delivery, transfer, mix, 5 min); 3. DCC (10% in CH$_2$Cl$_2$, (delivery and mix, 180 min); 4. CH$_2$Cl$_2$ (2×wash, 1 or 2 min).

4. Active Ester Coupling: 1. CH$_2$Cl$_2$ (2×wash, 1 or 2 min); 2. amino acid solution in DMF (delivery, transfer, mix 360 min); 3. CH$_2$Cl$_2$ (2×wash, 1 or 2 min).

5. Final Wash: 1. CH$_2$Cl$_2$ (2×wash, 1 or 2 min); 2. i-PrOH (3×wash, 1 or 2 min); 3. DMF (3×wash, 1 or 2 min); 4. CH$_2$Cl$_2$ (3×wash, 1 or 2 min).

6. Wash after TFA Treatment: 1. CH$_2$Cl$_2$ (2×wash, 1 or 2 min); 2. i-PrOH (3×wash, 1 or min); CH$_2$Cl$_2$ (3×wash, 1 or 2 min).

7. Acetylation: 1. CH$_2$Cl$_2$ (2×wash, 1 or 2 min); 2. 10% Ac$_2$O and Pyr in CH$_2$Cl$_2$ (1×wash, 1 or 2 min); 3. 10% Ac$_2$O and 10% Pyr in CH$_2$Cl$_2$ (acetylation, 20 min); 4. CH$_2$Cl$_2$ (2×wash, 1 or 2 min).

The first amino acid was attached to the resin by the program sequence 2-3-5. Before placing the resin into the reaction vessel, the resin was washed twice in a separatory funnel with 25 ml of CH$_2$Cl$_2$/g resin to remove the fine particles. In all couplings, usually a 3-4 fold excess of the Boc- amino acid over the nitrogen content of the resin (nitrogen content was about 0.5 meq/g dry resin) was used. This procedure generally resulted in a complete coupling reaction. If a positive ninhydrin color reaction was observed, a second coupling using an excess of the amino acid derivative was performed (program sequence 3-5). Then, the resin was acetylated (program sequence 7-5).

The next amino acid was attached by the program sequence 1-6-2-3-5. For DCC coupling, all amino acids were dissolved in CH$_2$Cl$_2$. To dissolve BOC-Trp, it was necessary to add 10% DMF to the suspension. Gln was coupled to the resin by its BocGlnONP derivative using the active ester coupling program sequence 1-6-2-4-5. The Boc-GlnONP was dissolved in DMF and a few mg of 1-hydroxybenzotriazole was added as a catalyst. The volume of the solvents and the reagents used for the washing and the performing of the chemical reactions was about 10 ml/g resin. The acetylation mixture was freshly prepared before each use.

Cleavage of the Peptides from the Resin

After all of the amino acids had been coupled, the peptide resin was dried overnight, in vacuo, by an oil pump. The resin was then treated with double-distilled and dried (over CoF$_3$) liquid hydrogen fluoride (10 ml/g resin) containing 10–25% distilled anisole for 1 hr at 0° C. Then, the HF was evaporated under reduced pressure and the residue was dried overnight, in vacuo, by an oil pump. The mixture was then extracted twice with EtOAc (25 ml/g resin), and then twice with 25 ml of 12% HOAc, and once with 25 ml distilled, deionized water. The combined aqueous solution was lyophilized to yield the crude peptide.

Purification of the Crude Peptide

Gel Filtration 220 mg of the crude peptide was applied to a column of Sephadex G-25 (100×2.5 cm) which had been equilibrated with 12% HOAc, and then the chromatography was done with the same solvent. Fractions of 10 ml were collected. The peptide was detected by spotting samples of the individual fractions on silica gel plates and chromatographing them in solvent system V. The fractions containing the product in a partially purified state were pooled and lyophilized. The yields were in the range of 76–120 mg.

Column Chromagraphy on Silica Gel

The above lyophilized material was applied to a column of silica gel (1×60cm), which had been equilibrated with a solvent system V and then the chromatography was done in the same solvent. Fractions of 4 ml were collected. The peptides, in general, were in elutes of fractions 30–40. The fractions which contained the pure or nearly pure peptide were collected and lyophilized. If the peptide was not sufficiently pure, it was further purified on the same column using the same solvent mixture. The yield ranged from 20–50%.

High Pressure Liquid Chromatography

The HPLC was performed on a Waters Liquid Chromatograph equipped with a Waters 660 solvent programmer. The samples were chromatographed ona chrompak Lichrosorb RP $C_{18}$ column (5u)(4.6×250 mm). For elution of the analogs a linear gradient from 20–100% of solvent B in 25 min. was used (solvent A:0.1 M K phosphate buffer, pH 3.0; solvent B: 30% solvent A, 70% $CH_3CH$). The flow rate was 2.10 ml/min; 10ul of a 0.1% solution of the peptide was injected. The eluted peptide was detected by its UV-absorbance at 206 mm.

Amino acid analysis

The acid analysis was performed on a Beckman Model 119 Automatic Amino Acid Analyzer. The peptides were hydrolyzed for 24 hours in a sealed glass tube at 110° C. in 6N HCl. The mixture was then dried, in vacuo. The residue was dissolved in 1.5 ml of sodium citrate buffer, pH 2.2 and 0.2 ml of the solution was applied to the analyzer.

Optical rotation

The optical rotation ($\alpha D$) was measured at room temperature with a Perkin Elmer 141 Polarimeter. All peptides were dissolved in 12% HOAC (10 mg/ml or 5 mg/ml) or in MeOH.

The Determination of Purity and The Characterization

The following procedures were used for determining the purity of all the synthetic analogs: thin layer chromatography in five solvents; amino acid analysis; optical rotation; high pressure liquid chromatography.

The TLC was performed on 0.25 mm silica gel plates 60F 254 in the solvent systems I–V, as defined supra. The spots were visualized with chlorine-o-tolidine reagent.

DATA

The amino acid analytical data are:
D-Pal$^6$-LHRH:
  Ser 0.88(1), Glu 1.00(1), Pro 1.01(1),
  Gly 1.02(1), Leu 1.02(1), Tyr 1.02(1),
  His 0.96(1), Arg 1.00(1), Trp(+), Pal(+).
D-Qal$^6$-LHRH:
  Ser 0.82(1), Glu 0.89(1), Pro 1.15(1),
  Gly 1.13(1), Leu 1.07(1), Tyr 0.94(1),
  His 0.89(1), Arg 1.11(1), Trp(+), Qal(+).
The chromatographic data are in Table I.

TABLE I

| | Chromatographic Data | | | | | |
|---|---|---|---|---|---|---|
| | $R_f$ in solvent | | | | Retention time in | Purity |
| Analog | I | II | III | IV | V | HPLC | (HPLC) |
| D-Pal$^6$-LHRH | 0.83 | 0 | 0.60 | 0.44 | 0.19 | 7.2 min. | 96% |
| D-Qal$^6$-LHRH | 0.93 | 0.13 | 0.65 | 0.40 | 0.25 | 8.6 min. | 94% |

Analogs of D-3 Pal$^6$-LHRH (1, 2, and 3)

The following three analogs of D-3 Pal$^6$-LHRH were similarly synthesized and purified as:
1. pryoGlu-His-Trp-Ser-Tyr-D-3-Pal-Leu-Arg-Pro-NHC$_3$H$_7$
2. pryoGlu-His-Trp-Ser-Tyr-D-3-Pal-Leu-Arg-Pro-NHC$_2$H$_5$
3. pryoGlu-His-Trp-Ser-Tyr-D-3-Pal-Leu-Arg-Pro-NHCH$_3$

TABLE II

The Characterization of Analogs 1, 2, and 3

| Purification Method | HPLC Data min. purity | | Amino Acid Data | | TLC ($R_f$) Solvent System | | | | |
|---|---|---|---|---|---|---|---|---|---|
| | | | | | I | II | III | IV | V |
| 1. (I,II,III) | 18.4 | 19% | Ser 1.05(1) | His 1.03(1) | 0.98 | 0 | 0.83 | 0.81 | 0.28 |
| | | | Glu 1.21(1) | Trp(+) | | | | | |
| | | | Pro 1.11(1) | Arg 1.20(1) | | | | | |
| | | | Leu 1.16(1) | D-3-Pal(+) | | | | | |
| | | | Tyr 1.25(1) | NH$_2$C$_3$H$_7$(+) | | | | | |
| 2. (I,II,III) | 16.1 | 99% | Ser 0.68(1) | His 1.00(1) | 0.98 | 0 | 0.83 | 0.78 | 0.20 |
| | | | Glu 0.87(1) | Trp(+) | | | | | |
| | | | Pro 0.86(1) | Arg .87(1) | | | | | |
| | | | Leu 0.77(1) | D-3-Pal(+) | | | | | |
| | | | Tyr 0.86(1) | C$_2$H$_5$NH$_2$(+) | | | | | |
| 3. (I,II,III) | 15.8 | 99% | Ser 0.90(1) | His 1.00(1) | 0.98 | 0 | 0.80 | 0.75 | 0.16 |
| | | | Glu 0.99(1) | Trp(+) | | | | | |
| | | | Pro 1.10(1) | Arg 1.04(1) | | | | | |
| | | | Leu 0.92(1) | D-3-Pal(1) | | | | | |

TABLE II-continued
The Characterization of Analogs 1, 2, and 3

| Purification Method | HPLC Data min. purity | Amino Acid Data | TLC ($R_f$) Solvent System | | | | |
|---|---|---|---|---|---|---|---|
| | | | I | II | III | IV | V |
| | | Tyr 1.05(1) $CH_3NH_2$(+) | | | | | |

The data in Table III are from the radioreceptor assay and allow a comparison of D-Qal[6]-LHRH with three of the known super agonists. This assay shows that the D-Qal[6]-LHRH is comparable with the three known super agonists for the potency of binding at a receptor and is substantially more effective than LHRH itself.

TABLE III
Radioreceptor Assay

| | Relative Potency vis-a-vis LHRH | Relative Potency vis-a-vis D-Lys[6]-LHRH-ethylamide |
|---|---|---|
| D-Lys[6]-LHRH-ethylamide | 0.015:1 | — |
| D-Qal[6]-LHRH | 0.020:1 | 1.36:1 |
| D-Trp[6]-LHRH | 0.011:1 | 0.72:1 |
| D-Trp[6] Pro[9] Net-LHRH | 0.013:1 | 0.86:1 |
| LHRH | — | 67.5:1 |

Receptor assay was performed by a modification of the method of Marshall, J. C., et al. Preparation of Biologically Active. I. LHRH Suitable for Membrane Binding Studies. *Proc. Soc. Exptl. Biol.* 149, 351 (1975).

The data in Tables IV and V are from the in vitro assay of the peptides with the pituitary incubate. This assay measures the release of LH and FSH in an in vitro system with pituitary cells from 21 day old rats. See, Bowers, C. Y. et al. on the inhibitory effects of leutinizing hormone releasing hormone analogs. *Endocrinology*, 106: 674 (1980).

The abbreviations are as follows: sc-subcutaneous, SEM-standard error of the means; NS-not significant; ng-nanogram, and ml-milliliter. The p value represents the population coefficient p (rho) which signifies whether a sample coefficient is significant or a chance deviation from zero.

The data in Table IV show that D-Pal[6]-LHRH and D-Qal[6]-LHRH are essentially equivalent in activity for the release of LH at 0.1 ng and the same essential equivalents at this dosage was revealed for the release of FSH.

Comparable assays have shown that D-Qal[6]-LHRH and D-Trp[6]-LHRH were essentially equipotent. On this basis, D-Pal[6]-LHRH and D-Trp[6]-LHRH can also be considered essentially equipotent.

TABLE IV
In Vitro Pituitary Incubate Assay
21 Day Old Female Rat

| Peptide | Dosage ng/ml medium | LH ng/ml medium ± SEM | p value | | medium ± SEM | p value | |
|---|---|---|---|---|---|---|---|
| LHRH | — | −8 ± 11 | | | 588 ± 233 | — | |
| | 0.03 | 52 ± 20 | <.02 | | 638 ± 292 | NS | |
| | 0.1 | 214 ± 30 | <.001 | | 266 ± 235 | <.001 | — |
| | 0.3 | 771 ± 162 | <.001 | | 4556 ± 752 | <.001 | — |
| | 1.0 | 1434 ± 156 | <.001 | | 8063 ± 943 | <.001 | — |
| D-Pal[6]-LHRH | 0.03 | 73 ± 10 | <.001 | NS* | 1062 ± 394NS | NS** | |
| | 0.1 | 345 ± 72 | <.001 | NS* | 3109 ± 486 | <.001 | NS** |
| | 0.3 | 811 ± 182 | <.001 | NS* | 5126 ± 967 | <.001 | NS** |
| | 1.0 | 1439 ± 233 | <.001 | NS* | 9637 ± 1490 | <.001 | NS** |
| D-Qal[6]-LHRH | 0.03 | 47 ± 22 | <.05 | NS* | 994 ± 181 | NS | NS** |
| | 0.1 | 335 ± 37 | <.001 | .02* | 3364 ± 364 | <.001 | NS** |
| | 0.3 | 611 ± 102 | <001 | NS* | 5069 ± 751 | <.001 | NS** |

*Versus data for LHRH
**Versus data for FSH
Note: mean of 9 ± SEM

TABLE V
In Vitro Pituitary Incubate Assay
21 Day Old Female Rat

| Peptide | Dosage ng/ml medium | LH ng/ml medium ± SEM | p value | FSH ng/ml medium ± SEM | p value |
|---|---|---|---|---|---|
| LHRH | — | −31 ± 63 | — | 156 ± 148 | — |
| | .01 | | | | |
| | .03 | 33 ± 24 | NS | 598 ± 137 | NS |
| | .10 | 206 ± 42 | <.01 | 794 ± 52 | <.001 |
| | .30 | 892 ± 92 | <.001 | 2709 ± 252 | <.001 |
| D-Qal[6]-LHRH | .01 | 104 ± 79 | NS | 625 ± 238 | NS |
| | .03 | 79 ± 30 | NS | 638 ± 77 | <.01 |
| | .10 | 647 ± 39 | <.001 | 1890 ± 135 | <.001 |
| D-Trp[6]-LHRH | .01 | 68 ± 31 | NS | 450 ± 64 | NS |
| | .03 | 209 ± 74 | .02 | 929 ± 207 | <.01 |
| | .10 | 646 ± 69 | <001 | 1714 ± 224 | <.001 |

TABLE V-continued

| | | In Vitro Pituitary Incubate Assay 21 Day Old Female Rat | | | |
|---|---|---|---|---|---|
| Peptide | Dosage ng/ml medium | LH ng/ml medium ± SEM | p value | FSH ng/ml medium ± SEM | p value |
| | | Mean of 9 ± SEM | | | |

Tables VI–XI summarize assays of LHRH and D-Pal[6]-LHRH for the release of the leutinizing hormone (LH) and the follicle stimulating hormone (FSH). D-Pal[6]-LHRH significantly released LH at a dosage of 5 ng in contrast to LHRH which was inactive at 15 ng. Correcting for the level of LH in the system before addition of the peptides, it is evident that the D-Pal[6]-LHRH released almost 50 times as much LH as did LHRH at the dosage of 50 ng.

At a dosage of 15 ng, D-Pal[6]-LHRH released 1270±140 ng FSH in contrast to LHRH which released only 572±68 ng. In vivo rat assay performed by a modification of the method of Bowers, C. Y. et al. *Endocrinology*, 106, 674 (1980). 21 day old female rats were injected sc with saline or peptide. Blood samples for the RIAs of LH and FSH were collected at +15, +60, +120, or +180 minutes. (Table VI–XI).

TABLE VI

In Vivo Assay in Rats For Release of LH and FSH

| Peptide | Dosage ng/rat sc | Serum LH ng/ml ± SEM | p value | Serum FFSH ng/ml ± SEM | p value |
|---|---|---|---|---|---|
| LHRH | — | 0.9 ± 0.7 | — | 227 ± 47 | — |
| | 15 | 1.3 ± 0.2 | NS | 475 ± 43 | <.01 | — |
| | 50 | 3.2 ± 0.3 | <.02 | — | 572 ± 68 | .01 | — |
| | 150 | 12 ± 3 | <.01 | | 839 ± 73 | <.001 |
| D-Pal[6]-LHRH | 1.75 | 1.5 ± 0.3 | NS | | 471 ± 128 | NS |
| | 5 | 7 ± 1 | <.001 | | 738 ± 71 | <.001 |
| | 15 | 43 ± 7 | <.001 | <.001 | 1270 ± 140 | <.001 | <.001 |
| | 50 | 103 ± 8 | <.001 | <.001 | 2267 ± 342 | <.001 | <.001 |
| | | Mean of 9 ± SEM | | | |

TABLE VII

Assay in Rats for Release of LH and FSH

| Peptide | Dosage mg/rat sc | LH ng/ml ± 15 min | Serum ± SEM ± 60 min | p value ± 15 min | p value ± 60 min |
|---|---|---|---|---|---|
| LHRH | — | 1.6 ± 9 | 1.1 ± 0.5 | — | — |
| | 100 | 49 ± 10 | 5.5 ± 0.9 | <.001 | <.01 |
| D-Qal[6]-LHRH | 10 | 10.5 ± 2 | 49 ± 14 | <.01 | <.01 |
| | 100 | 37 ± 5 | 226 ± 36 | <.001 | <.001 |
| D-Trp[6]-LHRH | 10 | | 31 ± 6 | | <.001 |
| | 100 | 51 ± 10 | 259 ± 34 | <.001 | <.001 |
| D-Trp[6]Pro[9]NET | 100 | 59 ± 10 | 228 ± 41 | <.001 | <.001 |

TABLE VIII

IN VIVO Assay in Rats for Release of LH and FSH

| Peptide | Dosage ng/rat sc | Serum LH ng/ml ± SEM | p value | Serum FSH ng/ml ± SEM | p value |
|---|---|---|---|---|---|
| — | — | 1.7 ± 0.9 | — | 315 ± 186 | — |
| LHRH | 15 | 21.0 ± 4.0 | — | <.001 | 1147 ± 489 | NS |
| LHRH | 50 | 53.9 ± 9.0 | | <.001 | 2228 ± 448 | — | <.01 |
| LHRH | 150 | 62.0 ± 21.0 | — | <.02 | 1536 ± 172 | — | <.001 |
| D-Pal[6]-LHRH | 15 | 36 ± 9 | NS | <.01 | 1711 ± 644 | NS | NS < .05 |
| D-Pal[6]-LHRH | 150 | 111 ± 16 | NS | <.001 | 1591 ± 588 | NS | NS .05 |
| ±60 min after injection of peptide or saline(−) | | | | | |
| — | — | 1.3 ± 0.2 | <.05 | — | 815 ± 64 | <.001 | — |
| LHRH | 150 | 39.0 ± 17 | — | <.05 | 2448 ± 209 | — | <.001 |
| D-Pal[6]-LHRH | 15 | 81.0 ± 17 | NS | <.001 | 1992 ± 379 | NS | .01 |
| D-Pal[6]-LHRH | 150 | 106.0 ± 3 | <.01 | <.001 | 6432 ± 2216 | NS | .02 |
| D-Qal[6]-LHRH | 15 | 68.0 ± 19 | NS | <.01 | 3610 ± 363 | <.05 | <.001 |
| D-Qal[6]-LHRH | 150 | 118.0 ± 3 | .001 | <.001 | 6694 ± 2619 | NS | <.05 |

Mean of 5-6 ± SEM

TABLE IX

IN VIVO Assay in Rats for Release of LH and FSH

| Peptide | Dose ng/rat | Serum LH ng/ml SEM | p value | Serum FSH ng/ml SEM | p value |
|---|---|---|---|---|---|
| — | — | 1.2 ± 0.9 | | 311 ± 36 | |
| LHRH | 50 | 5 ± 0.5 | — | 909 ± 118 | — |

TABLE IX-continued

IN VIVO Assay in Rats for Release of LH and FSH

| Peptide | Dose ng/rat | Serum LH ng/ml SEM | p value | Serum FSH ng/ml SEM | p value |
|---|---|---|---|---|---|
| | 150 | 17 ± 3 | — | 1076 ± 185 | — |
| 21435 | 50 | 0.2 ± 0.1 | <.001 | 395 ± 116 | <.05 |
| | 150 | 2 ± 1 | NS | 429 ± 132 | <.05 |
| 21436 | 50 | 116 ± 20 | <.001 | 3471 ± 229 | <.001 |
| | 150 | 144 ± 37 | <.01 | 1458 ± 424 | NS |
| 21437 | 50 | 47 ± 8 | <.001 | 1707 ± 518 | NS |
| | 150 | 111 ± 26 | <.01 | 2799 ± 783 | NS |
| 20723 | 50 | 120 ± 16 | <.001 | 3099 ± 361 | <.001 |
| | 150 | 122 ± 19 | <.001 | 3064 ± 677 | <.05 |
| | 50 | 71 ± 8 | <.001 | 1273 ± 279 | NS |
| | 150 | 151 ± 17 | <.001 | 3472 ± 538 | <.01 |

21435 D-3-Pal$^6$-LHRH—C$_3$H$_7$
21436 D-3-Pal$^6$-LHRH—C$_2$H$_5$
21437 D-3-Pal$^6$-LHRH—CH$_3$
21423 D-3-Pal$^6$-LHRH
20700 D-3-Qal$^6$-LHRH
Mean of 6 ± SEM P values compared to respective dose of LHRH. Blood sample at ±60 minutes after injection of saline or peptide sc.

TABLE X

IN VIVO Assay in Rats for Release of LH and FSH: 21 Day-Old Females

| Peptide | Dose ng/rat sc | LH ng/ml Serum ±SEM at +120 min | p value | FSH ng/ml Serum ±SEM at +120 min | P value |
|---|---|---|---|---|---|
| | — | 0.2 ± 0.1 | — | 332 ± 50 | — |
| D-Pal$^6$-NH—C$_2$H$_5$ | 50 | 291 ± 11 | — | 4692 ± 393 | — |
| D-Pal$^6$-NH—C$_2$H$_5$ | 150 | 278 ± 14 | — | 4811 ± 782 | — |
| D-Pal$^6$-LHRH | 50 | 111 ± 26 | <.001 | 3251 ± 485 | NS |
| D-Pal$^6$-LHRH | 150 | 216 ± 46 | NS | 5293 ± 686 | NS |

TABLE XI

IN VIVO Assay in Rats for Release of LH and FSH 21-Day Old Females

| Peptide | Dose-sc | +2 hrs LH ± SEM ng/ml serum | p value | +3 hrs LH ± SEM ng/ml serum | p value |
|---|---|---|---|---|---|
| 0.15 | — | <0.1 | | 0.24 ± 0.14 | |
| LHRH | 150 ng | .18 ± 0.07 | <.001 | 0.66 ± 0.46 | <.001 |
| 20723 | 50 ng | 108 ± 17 | NS | 20 ± 2.3 | NS |
| 20723 | 150 ng | 144 ± 27 | — | 38 ± 6.3 | — |
| 21436 | 150 ng | 237 ± 52 | NS | 106 ± 13 | <.01 |
| 27000 | 150 ng | 156 ± 7 | NS | 104 ± 23 | <.05 |
| CDB 8600 | 150 ng | 230 ± 41 | NS | 117 ± 9 | <.001 |
| 83-256-50 | 150 ng | 184 ± 29 | NS | 103 ± 9 | <.001 |

| Peptide | Dose-sc | FSH ± SEM ng/ml serum | p value | FSH ± SEM ng/ml serum | p value |
|---|---|---|---|---|---|
| 0.1% gel | — | 147 ± 19 | <.001 | 361 ± 38 | <.001 |
| LHRH | 150 ng | 337 ± 20 | <.001 | 487 ± 72 | <.001 |
| 20723 | 50 ng | 1727 ± 222 | NS | 1312 ± 163 | NS |
| 20723 | 150 ng | 2362 ± 293 | — | 1617 ± 143 | — |
| 21436 | 150 ng | 2415 ± 361 | NS | 2205 ± 298 | NS |
| 27000 | 150 ng | 2211 ± 160 | NS | 2376 ± 529 | NS |
| CDB 8600 | 150 ng | 2332 ± 388 | NS | 2065 ± 151 | NS |
| 83-256-50 | 150 ng | 2260 ± 294 | NS | 1763 ± 148 | NS |

Mean 5-6 ± SEM
20723 pyroGlu-His-Trp-Ser-Tyr-D-Pal*-Leu-Arg-Pro-Gly-NH$_2$
21436 pyroGlu-His-Trp-Ser-Tyr-D-Pal*-Leu-Arg-Pro-EA**
27000 pyroGlu-His-Trp-Ser-Tyr-D-Qal***-Leu-Arg-Pro-Gly-NH$_2$
CDB 8600 pyroGlu-His-Trp-Ser-Tyr-D-Trp-Leu-Arg-Pro-Gly-NH$_2$
83-256-50 pyroGlu-His-Trp-Ser-Tyr-D-Trp-Leu-Arg-Pro-EA**
*D-3-Pal = 3-(3-Pyridyl)-D-Ala
**EA = ethylamide
***D-3-Qal = 3-(3-Quinolyl)-D-Ala

What is claimed:
1. pyroGlu-His-Trp-Ser-Tyr-D-3-Qal-Leu-Arg-Pro-Gly-NH$_2$.
2. pyroGlu-His-Trp-Ser-Tyr-D-3-Qal-Leu-Arg-Pro-NHCH$_3$.
3. pyroGlu-His-Trp-Ser-Tyr-D-3-Qal-Leu-Arg-Pro-NHC$_2$H$_5$.
4. pyroGlu-His-Trp-Ser-Tyr-D-3-Qal-Leu-Arg-Pro-NHC$_3$H$_7$.

* * * * *